United States Patent
Singleton et al.

(10) Patent No.: US 6,537,945 B2
(45) Date of Patent: Mar. 25, 2003

(54) HIGHLY ACTIVE FISCHER-TROPSCH CATALYST HAVING INCREASED THERMAL STABILITY

(75) Inventors: Alan H. Singleton, Baden, PA (US); Rachid Oukaci, Gibsonia, PA (US)

(73) Assignee: Energy International Corporation, Pittsburgh, PA (US)

( * ) Notice: Subject to any disclaimer, the term of this patent is extended or adjusted under 35 U.S.C. 154(b) by 0 days.

(21) Appl. No.: 09/810,790

(22) Filed: Mar. 16, 2001

(65) Prior Publication Data
US 2001/0031793 A1 Oct. 18, 2001

Related U.S. Application Data

(62) Division of application No. 09/528,163, filed on Mar. 17, 2000, now Pat. No. 6,255,358.

(51) Int. Cl.[7] .................................................. B01J 23/40
(52) U.S. Cl. ........................ 502/327; 502/415; 502/439
(58) Field of Search ................................. 502/327, 303, 502/439, 414, 415

(56) References Cited

U.S. PATENT DOCUMENTS

| | | | | |
|---|---|---|---|---|
| 4,088,671 A | * | 5/1978 | Kobylinski | 260/449.6 R |
| 4,399,234 A | * | 8/1983 | Beuther et al. | 518/715 |
| 4,493,905 A | * | 1/1985 | Beuther et al. | 502/325 |
| 4,585,798 A | * | 4/1986 | Beuther et al. | 518/715 |
| 4,670,414 A | * | 6/1987 | Kobylinski et al. | 502/174 |
| 4,717,702 A | * | 1/1988 | Beuther et al. | 502/303 |
| 4,822,824 A | * | 4/1989 | Iglesia et al. | 518/709 |
| 5,023,276 A | * | 6/1991 | Yarrington et al. | 514/703 |
| 5,140,050 A | * | 8/1992 | Mauldin et al. | 518/715 |
| 5,145,876 A | * | 9/1992 | Shutt | 518/715 |
| 5,292,705 A | * | 3/1994 | Mitchell | 502/325 |
| 5,856,365 A | * | 1/1999 | Zennaro et al. | 518/715 |
| 5,939,350 A | * | 8/1999 | Singleton et al. | 502/230 |
| 6,100,304 A | * | 8/2000 | Singleton et al. | 518/715 |
| 6,149,799 A | * | 11/2000 | Raybaud et al. | 208/49 |
| 6,182,443 B1 | * | 2/2001 | Jarvis et al. | 60/274 |
| 6,191,066 B1 | * | 2/2001 | Singleton et al. | 502/332 |
| 6,262,132 B1 | * | 7/2001 | Singleton et al. | 518/715 |
| 6,271,432 B2 | * | 8/2001 | Singleton et al. | 585/700 |

* cited by examiner

Primary Examiner—Stanley G. Silverman
Assistant Examiner—Cam N. Nguyen
(74) Attorney, Agent, or Firm—Fellers, Snider, Blankenship, Bailey & Tippens

(57) ABSTRACT

A highly active Fischer-Tropsch catalyst having increased thermal stability. The catalyst comprises a γ-alumina support doped with an amount of lanthana oxide, barium oxide, or a combination thereof effective for increasing the thermal stability of the catalyst in a slurry bubble column reaction system while maintaining or increasing the activity of the catalyst for Fischer-Tropsch synthesis.

6 Claims, 2 Drawing Sheets

EFFECT OF DOPING ON THERMAL STABILITY OF ALUMINA

EFFECT OF SUPPORT DOPANTS ON ACTIVITY OF RuCo/Al$_2$O$_3$ CATALYSTS IN SBCR

HIGHLY ACTIVE FISCHER-TROPSCH CATALYST HAVING INCREASED THERMAL STABILITY

This application is a divisional of copending application Ser. No. 09/528,163 filed Mar. 17, 2000, U.S. Pat. No. 6,255,358 B1, issued Jul. 3, 2001.

BACKGROUND OF THE INVENTION

1. Technical Field

This invention relates to alumina supported cobalt catalysts having an improved stability and high activity for Fischer-Tropsch (F-T) synthesis conducted in a slurry bubble column and other three-phase type reactors.

2. Background

In Fischer-Tropsch processes, synthesis gases comprising carbon oxides and hydrogen are reacted in the presence of Fischer-Tropsch catalysts to produce liquid hydrocarbons. Fischer-Tropsch synthesis processes are most commonly conducted in fixed bed, gas-solid or gas-entrained fluidized bed reaction systems, fixed bed reaction systems being the most commonly used. It is recognized in the art, however, that slurry bubble column reactor systems offer tremendous potential benefits over these commonly used Fischer-Tropsch reaction systems.

As mentioned above, the synthesis gas, or "syngas," used in Fischer-Tropsch processes is typically a mixture consisting primarily of hydrogen and carbon oxides. Syngas is typically produced, for example, during coal gasification. Processes are also well known for obtaining syngas from other hydrocarbons, including natural gas. U.S. Pat. No. 4,423,265 to Chu et al. notes that the major processes for producing syngas depend either upon the partial combustion of a hydrocarbon fuel with an oxygen-containing gas or the reaction of the fuel with steam, or on a combination of these two reactions. U.S. Pat. No. 5,324,335 to Benham et al., explains the two primary methods (i.e., steam reforming and partial oxidation) for producing syngas from methane. The Encyclopedia of Chemical Technology, Second Edition, Volume 10, pages 3553–433 (1966), Interscience Publishers, New York, N.Y. and Third Edition, Volume 11, pages 410–446 (1980), John Wiley and Sons, New York, N.Y. is said by Chu et al. to contain an excellent summary of gas manufacture, including the manufacture of synthesis gas.

It has long been recognized that syngas can be converted to liquid hydrocarbons by the catalytic hydrogenation of carbon monoxide. The general chemistry of the Fischer-Tropsch synthesis process is as follows:

  (1)

  (2)

The types and amounts of reaction products, i.e., the lengths of carbon chains, obtained via Fischer-Tropsch synthesis vary dependent upon process kinetics and the catalyst selected.

Many attempts at providing active catalysts for selectively converting syngas to liquid hydrocarbons have previously been disclosed. U.S. Pat. No. 5,248,701 to Soled et al., presents an over-view of relevant prior art. The two most popular types of catalysts heretofore used in Fischer-Tropsch synthesis have been iron-based catalysts and cobalt-based catalysts. U.S. Pat. No. 5,324,335 to Benham et al. discusses the fact that iron-based catalysts, due to their high water gas shift activity, favor the overall reaction shown in (2) above, while cobalt-based catalysts tend to favor reaction scheme (1).

Recent advances have provided a number of catalysts active in Fischer-Tropsch synthesis. Besides iron and cobalt, other Group VIII metals, particularly ruthenium, are known Fischer-Tropsch catalysts. The current practice is to support such catalysts on porous, inorganic refractory oxides. Particularly preferred supports include silica, alumina, silica-alumina, and titania. In addition, other refractory oxides selected from Groups III, IV, V, VI and VIII may be used as catalyst supports.

The prevailing practice is to also add promoters to the supported catalyst. Promoters can include ruthenium (when not used as the primary catalyst component), rhenium, hafnium, cerium, and zirconium. Promoters are known to increase the activity of the catalyst, sometimes rendering the catalyst three to four times as active as its unpromoted counterpart.

Contemporary cobalt catalysts are typically prepared by impregnating the support with the catalytic material. As described in U.S. Pat. No. 5,252,613 to Chang et al., a typical catalyst preparation may involve impregnation, by incipient wetness or other known techniques, of, for example, a cobalt nitrate salt onto a titania, silica or alumina support, optionally followed or preceded by impregnation with a promoter material. Excess liquid is then removed and the catalyst precursor is dried. Following drying, or as a continuation thereof, the catalyst is calcined to convert the salt or compound to its corresponding oxide(s). The oxide is then reduced by treatment with hydrogen, or a hydrogen-containing gas, for a period of time sufficient to substantially reduce the oxide to the elemental or catalytic form of the metal. U.S. Pat. No. 5,498,638 to Long points to U.S. Pat. Nos. 4,673,993, 4,717,702, 4,477,595, 4,663,305, 4,822,824, 5,036,032, 5,140,050, and 5,292,705 as disclosing well known catalyst preparation techniques.

As also mentioned above, Fischer-Tropsch synthesis has heretofore been conducted primarily in fixed bed reactors, gas-solid reactors, and gas-entrained fluidized bed reactors, fixed bed reactors being the most utilized. U.S. Pat. No. 4,670,472 to Dyer et al. provides a bibliography of several references describing these systems. The entire disclosure of U.S. Pat. No. 4,670,472 is incorporated herein by reference.

In contrast to these other hydrocarbon synthesis systems, slurry bubble column reactors are "three phase" (i.e., solid, liquid, and gas/vapor) reaction systems involving the introduction of a fluidizing gas into a reactor containing catalyst particles slurried in a hydrocarbon liquid. The catalyst particles are slurried in the liquid hydrocarbons within a reactor chamber, typically a tall column. Syngas is then introduced at the bottom of the column through a distributor plate, which produces small gas bubbles. The gas bubbles migrate up and through the column, causing beneficial agitation and turbulence, while reacting in the presence of the catalyst to produce liquid and gaseous hydrocarbon products. Gaseous products are captured at the top of the SBCR, while liquid products are recovered through a filter which separates the liquid hydrocarbons from the catalyst fines. U.S. Pat. Nos. 4,684,756, 4,788,222, 5,157,054, 5,348,982, and 5,527,473 reference this type of system and provide citations to pertinent patent and literature art. The entire disclosure of each of these patents is incorporated herein by reference.

It is recognized that conducting Fischer-Tropsch synthesis using a SBCR system could provide significant advantages. As noted by Rice et al. in U.S. Pat. No. 4,788,222, the potential benefits of a slurry process over a fixed bed process include better control of the exothermic heat produced by the Fischer-Tropsch reactions, as well as better maintenance of catalyst activity by allowing continuous recycling, recovery and rejuvenation procedures to be implemented. U.S. Pat. Nos. 5,157,054, 5,348,982, and 5,527,473 also discuss advantages of the SBCR process.

Normal operation of F-T synthesis leads to the buildup of carbonaceous deposits on a cobalt catalyst resulting in catalyst deactivation with time-on-stream, the amount of this major source of deactivation being related to the reaction conditions used. In general, cobalt catalysts may be regenerated by calcination at relatively high temperatures (burning off the carbon residues) followed by reduction. However, the successive exposure of these catalysts to high temperatures may result in a slow decrease of the support surface area followed by encapsulation of cobalt particles and the formation of harder to reduce or totally non-reducible cobalt-metal compounds. All these changes are associated with a decrease of the cobalt surface area accessible to reactants which results in a slow loss of activity after each regeneration cycle.

Alumina, one of the common oxides used as a support for cobalt-based F-T catalysts, is well known to be sensitive to the pretreatment temperatures and the amount of time it is subjected to high temperatures. The crystalline form of the alumina most commonly used as catalyst support is γ-alumina. It is generally obtained by dehydration of aluminum hydroxide (boehmite) by heating under suitable conditions (typically, 300–650° C.). Further heating, either during the pretreatment step, during the use of the catalyst or during catalyst regeneration may result in a slow and continuous loss of surface area and a slow conversion of the alumina from its γ-alumina phase to other forms (δ-alumina then θ-alumina) which have much lower surface areas. Finally, especially at very high temperatures, a collapse of the structure resulting in the formation of a dense, highly stable, low surface area α-alumina can occur.

It has been suggested by Condea/Vista and by R. Gaugin, M. Graulier, and D. Papee, "Thermally Stable Carriers," *Advances in Chemistry Series*, Vol. 143, p. 147 (1975) that the thermal stability of some γ-aluminas materials can be enhanced by incorporating into the alumina small amounts of divalent ions, such as calcium, magnesium, or barium or rare earth oxides such as lanthana. These are believed to occupy tetrahedral voids in the spinel and retard the diffusion of $Al^{3+}$ cations. However, the effects of such support additives on the activities and other characteristics of any catalysts formed therefrom are unknown. The activities and selectivities of Fischer-Tropsch catalysts, for example, are known to be extremely sensitive to changes in catalyst or support compositions.

SUMMARY OF THE INVENTION

The invention unexpectedly and surprisingly provides highly stable and highly active alumina supported cobalt catalysts for use in Fischer-Tropsch synthesis processes.

In another aspect, the inventive method comprises the step of reacting a synthesis gas in a slurry bubble column reactor system in the presence of a catalyst comprising a γ-alumina support, wherein the γ-alumina support includes an amount of lanthana or barium oxide effective for increasing the thermal stability of the catalyst.

Further objects, features, and advantages of the present invention will be apparent upon examining the accompanying drawings and upon reading the following detailed description of the preferred embodiments.

DETAILED DESCRIPTION OF THE PREFERRED EMBODIMENTS

Catalyst Compositions

Figure 1:
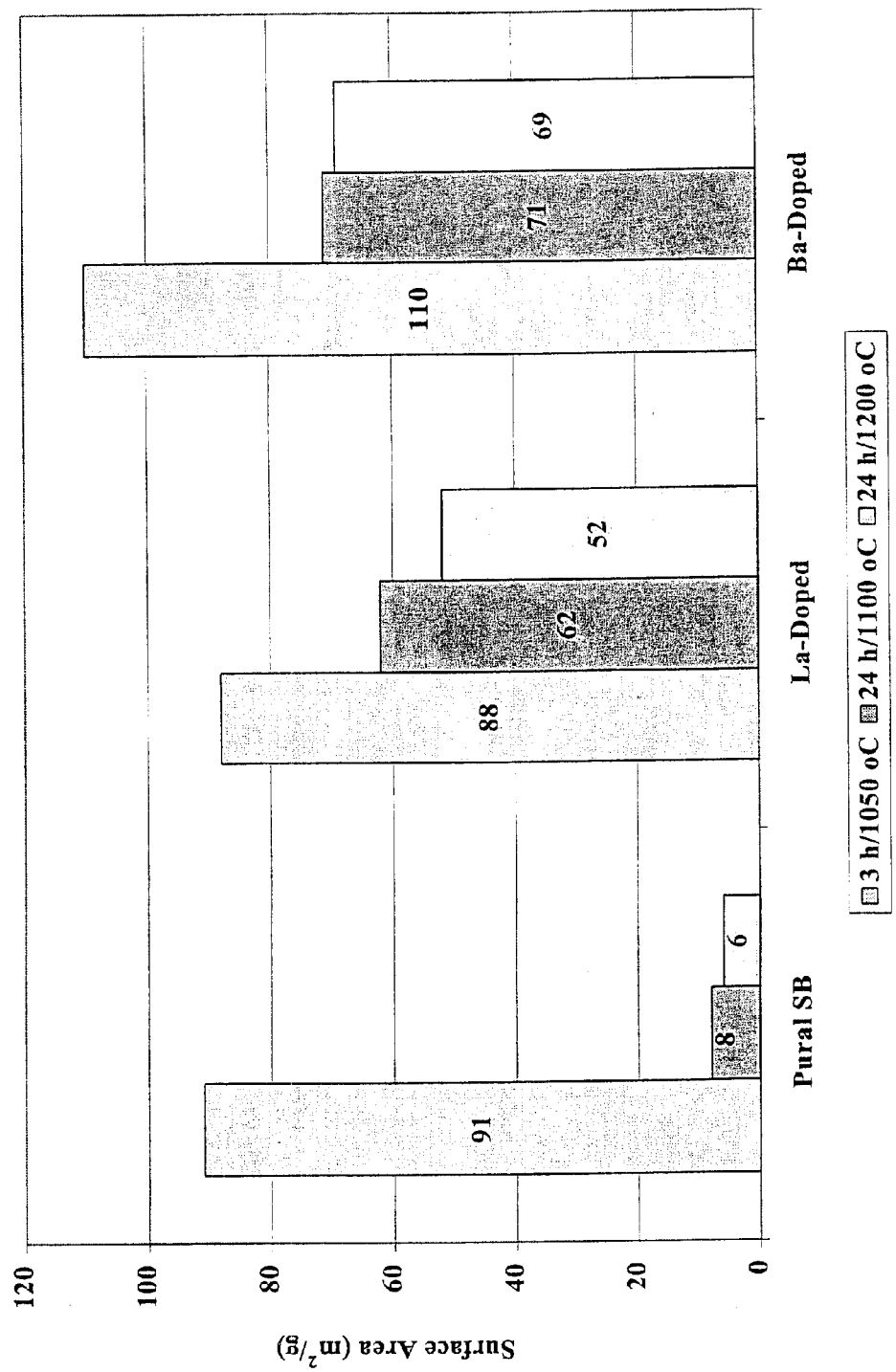
FIG. 1 provides a graph comparing the thermal stability of lanthanum- and barium-doped aluminas to the thermal stability of a more common non-doped alumina.

The present invention provides supported cobalt catalysts which are well suited for use in Fischer-Tropsch synthesis processes. These catalysts are particularly well suited for use in three-phase reactor processes. Examples of general catalyst compositions provided by the present invention include: (a) cobalt, without any promoter, preferably supported on doped γ-alumina; (b) cobalt, with one or more noble metal promoters, preferably supported on doped γ-alumina; (c) cobalt, promoted with both a noble metal promoter and one or more selectivity promoters (preferably an alkali or rare earth oxide), preferably supported on doped γ-alumina; and (d) cobalt, promoted with one or more selectivity promoters and without a noble metal promoter, preferably supported on doped γ-alumina. Examples of typical promoters include, but are not limited to, noble metals such as ruthenium, metal oxides such as oxides of zirconium, lanthanum, or potassium, and other oxides of elements from Groups IA, IIA, IVB, VB, and VIB.

Preferred catalyst compositions comprise (per 100 parts by weight of support): from about 10 to about 70 pbw cobalt; from about 0.1 to about 8 pbw ruthenium (when present); from about 0.1 to about 8 pbw potassium (when present); and from about 0.5 to about 8 pbw lanthana (when present). The catalyst can also include other promoter materials. We have discovered that, to obtain a particularly desirable combination of selectivity and activity, particularly in reaction systems such as slurry bubble column reactors, the catalysts will most preferably comprise (per 100 parts by weight of support): from about 15 to about 55 pbw (more preferably from about 20 to about 45 pbw) cobalt; from about 0.2 to about 1.5 pbw ruthenium (when present); from about 0.2 to about 1.0 pbw potassium (when present); and from about 0.5 to about 5.0 pbw (most preferably from about 0.9 to about 2.5 pbw) lanthana (when present).

The Catalyst Support

The catalyst support employed in the present invention is preferably a lanthanum or a barium doped γ-alumina support having: a low level of impurities, especially sulfur (preferably less than 100 ppm sulfur); a spheroidal shape; an average particle size in the range of from about 10 to about 150 μm (most preferably from about 20 to about 80 microns); a BET surface area, after calcination, in the range of from about 200 to about 260 $m^2/g$; and a porosity in the range of from about 0.4 to about 1.0 $cm^3/g$.

The alumina support is preferably produced from relatively high purity, synthetic boehmite. As discussed hereinbelow, the boehmite can be formed from aluminum alkoxide of the type obtained in the manufacture of synthetic fatty alcohols. Alternatively, suitable, high purity boehmite materials can be formed from aluminum alkoxide produced by alcohol/aluminum metal reaction processes.

The aluminum alkoxide is preferably hydrolyzed to produce high purity, synthetic, monohydrate alumina. Next, this material is preferably spray-dried to yield highly porous, spherical boehmite particles of relatively high surface area. The particulate boehmite material is preferably then sieved to remove fines and large particles so that a desired particle size range is obtained (most preferably from about 20 to about 80 microns). The sieved material is calcined to convert the boehmite particles to a γ-alumina support material having the desired surface area and porosity. The boehmite material will preferably be calcined at a temperature of at least 350° C. (more preferably from about 400° C. to about 700° C. and most preferably about 500° C.) for a period of from about 3 to about 24 hours (more preferably from about 5 to about 16 hours and most preferably about 10 hours). The desired calcination temperature is preferably reached by slowly heating the system at a rate of about 0.5–2.0° C./minute.

The $La_2O_3$ or BaO dopant will preferably be present in the γ-alumina support in an amount in the range of from about 1% to about 5% of $La_2O_3$ or BaO based on the total weight of the support. The dopant will more preferably be present in the support in an amount in the range of 2 to 3% by weight and will most preferably be present in an amount of about 3% by weight. The dopant can be added at substantially any time but will most preferably be added prior to crystallization of the boehmite.

As is well known to those skilled in the art, one of the ways of producing synthetic boehmite materials utilizes aluminum alkoxides recovered as byproducts of certain processes (e.g., the Ziegler Process) for manufacturing synthetic fatty alcohols. The Ziegler Process comprises the steps of: (1) reacting high purity alumina powder with ethylene and hydrogen to produce aluminum triethyl; (2) polymerizing ethylene by contacting it with the aluminum triethyl, thus resulting in the formation aluminum alkyls; (3) oxidizing the aluminum alkyls with air to produce aluminum alkoxides; and (4) hydrolizing the aluminum alkoxides to produce alcohols and an alumina byproduct.

In another process, aluminum alkoxide is formed by reacting an alcohol with a highly pure aluminum powder. The aluminum alkoxide is then hydrolyzed to produce an alcohol, which is recycled for use in the alkoxide formation step, and alumina. For purposes of the present invention, any desired amount of dopant, whether lanthanum and/or barium, can be included in the alumina product by, for example, adding a corresponding dopant alkoxide to, and co-hydrolyzing the dopant alkoxide with, the aluminum alkoxide formed in the first step of this process.

For comparison purposes, examples of commercially-supplied boehmite materials suitable for forming non-doped γ-alumina supports otherwise of the type employed in the present invention include the CATAPAL and PURAL aluminas supplied by Condea/Vista. These materials may contain up to 2000 ppm of titanium by weight, depending on the process used for their manufacture. The commercial materials of this type, which can be effective for making highly active F-T cobalt-based catalysts, do not always provide adequate thermal stability and may limit the number of reaction-regeneration cycles allowable during the overall life of these catalysts.

FIG. 1, reproduced from data obtained by Condea/Vista, shows the reported effect of lanthanum and barium doping on the thermal stability of aluminas. The doped aluminas contain about 3% by weight of lanthana and barium oxide, respectively. These results show that the surface area of the conventional (non-doped) alumina Pural SB decreases significantly when it is heated above 1000° C. for several hours. However, the doped aluminas did not undergo such a drastic decrease in surface area when subjected to the same heat treatment. Thus, the lanthana and barium oxide played a major role in improving the stabilities of these bare aluminas even at temperatures where the aluminas are expected to be converted to a α phase having a surface area of only a few $m^2/g$. Although F-T catalysts using these aluminas will not be subjected to such high temperatures, repeated regenerations even at much lower temperatures of the order of 300–500° C. may, eventually, also significantly decrease the surface areas of conventional, non-doped alumina supports.

Catalyst Preparation

The catalytic components of the preferred catalysts are preferably added to the support by totally aqueous impregnation using appropriate aqueous solution compositions and volumes to achieve incipient wetness of the support material with the desired metal loading(s). Promoted catalysts are most preferably prepared by totally aqueous co-impregnation. Examples of typical promoters include: noble metals; metal oxides such as oxides of Zr, La, K; and other oxides of elements from Groups IA, IIA, IVB, VB, and VIB.

In accordance with the present invention, the totally aqueous impregnation of cobalt onto the support, with or without one or more desired promoters, is preferably accomplished by the steps of: (a) calcining the alumina support in the manner described above; (b) impregnating the support with an aqueous solution of cobalt nitrate, or of cobalt nitrate and one or more promoter compounds (preferably one or more promoter-nitrates [e.g., ruthenium (III) nitrosyl nitrate] and/or promoter-chlorides [e.g., ruthenium III chloride], most preferably promoter-nitrates) using a sufficient quantity of the solution to achieve incipient wetness with a desired loading of cobalt and of any desired promoter(s); (c) drying the resulting catalyst precursor for about 5–24 hours at approximately 80–130° C., with moderate mixing, to remove solvent water and obtain a dried catalyst; and (d) calcining the dried catalyst in air or nitrogen by slowly raising the temperature of the system at a rate of about 0.5–2.0° C. per minute to approximately 250–400° C. and then holding for at least 2 hours to obtain the oxide form of the catalyst. Multiple impregnation/co-impregnation steps (b) can be used when higher cobalt loadings are desired.

As one example, a particularly preferred ruthenium-promoted cobalt catalyst is prepared according to the following procedure. First, the support, preferably a lanthanum or barium doped γ-alumina, is calcined at from about 400° C. to about 700° C., preferably about 500° C., for about 10 hours. The calcined support is then impregnated with an aqueous solution containing both cobalt nitrate $[Co(NO_3)_2\cdot 6H_2O]$ and ruthenium (III) nitrosyl nitrate $[Ru(NO)(NO_3)_3\cdot xH_2O]$ using an appropriate quantity to achieve incipient wetness with the desired loadings of cobalt and ruthenium. The resulting catalyst precursor is then dried for 5 hours at 115° C. with moderate stirring in order to remove the solvent water. The dried catalyst is then calcined in air by raising its temperature at a rate of 1° C./min to 300° C. and holding for at least 2 hours.

Catalyst Activation

To provide optimum performance, it is presently preferred that the catalyst be activated/reduced in a hydrogen-containing gas by slowly increasing the temperature of the catalyst, preferably at a rate of about 0.5–2.0° C./minute, to approximately 250–400° C. preferably about 350° C.) and holding at the desired temperature for at least 2 hours. After reduction, the catalyst is preferably cooled in flowing nitrogen.

The reducing gas preferably comprises from about 1% to 100% by volume hydrogen, with the remainder (if any) being an inert gas, typically nitrogen. The reducing gas is preferably delivered at a rate of about 2–4 (preferably about 3) liters per hour per gram of catalyst. The reduction procedure is preferably conducted in a fluidized bed reactor. The reduction procedure is most preferably conducted at conditions (i.e., temperature, flow rate, hydrogen concentration, etc.) effective to ensure that a very low water vapor partial pressure is maintained during the procedure.

The Fischer-Tropsch Reaction Process

The catalysts prepared and activated in accordance with the present invention can be employed in generally any Fischer-Tropsch synthesis process. For slurry bubble column and other three-phase reaction systems, the catalyst will preferably be slurried in a Fischer-Tropsch wax or in a synthetic fluid (e.g., a $C_{30}$ to $C_{50}$ range isoparaffin polyalphaolefin such as that available from Chevron under the name SYNFLUD) having properties similar to those of Fischer-Tropsch wax. The catalyst slurry will preferably have a catalyst concentration in the range of from about 5% to about 40% by weight based on the total weight of the slurry.

The synthesis gas feed used in the reaction process will preferably have a $CO:H_2$ volume ratio of from about 0.5 to about 3.0 and will preferably have an inert gas (i.e., nitrogen, argon, or other inert gas) concentration in the range of from 0 to about 60% by volume based on the total volume of the feed. The inert gas is preferably nitrogen.

Prior to initiating the reaction process, the activated catalyst will most preferably be maintained in an inert atmosphere. Before adding the catalyst thereto, the slurry fluid will preferably be purged with nitrogen or other inert gas to remove any dissolved oxygen. The slurry composition will also preferably be transferred to the reaction system under an inert atmosphere.

A particularly preferred SBCR reaction procedure comprises the steps of: (a) filling the SBCR, under an inert atmosphere, with the activated catalyst slurry; (b) heating and pressurizing the SBCR, under an inert atmosphere, to the desired pretreatment conditions (preferably a temperature in the range of from about 220° C. to about 250° C. and a pressure in the range of from about 50 to about 500 psig); (c) replacing the inert gas with hydrogen and holding the system at these conditions for from about 2 to about 20 hours; (d) purging the system with inert gas and lowering the reaction system temperature, if necessary, to a point at least about 10° C. below the desired reaction temperature; (e) carefully replacing the inert gas with the desired synthesis gas; and (f) heating and pressurizing the reaction system, as necessary, to a desired operating temperature, preferably in the range of from about 190° C. to about 300° C., and a desired operating pressure, preferably in the range of from about 50 to about 900 psig.

EXAMPLES

The following examples describe the preparation of various catalysts and the results obtained from testing these catalysts for conversion of synthesis gas into hydrocarbons. Before being tested, each catalysts was reduced in a pure hydrogen gas by slowly increasing the temperature of the catalyst, at a rate of about 1.0° C./minute, to about 350° C. and holding at this temperature for 10 hours. The hydrogen was delivered at a rate of about 3 liters per hour per gram of catalyst. After reduction, the catalyst was cooled in flowing nitrogen.

For the slurry bubble column reactor tests, the reduction procedure was conducted in a fluidized bed reactor. After cooling to ambient temperature, the catalyst was weighed, slurried in Synfluid and transferred to the SBCR under an inert atmosphere. All the F-T reaction tests in the SBCR were carried out at 230° C., 450 psig, 900 sl/hr syngas containing 60% nitrogen and having a $H_2/CO$ ratio of 2, using 15–25 g of reduced catalyst. The catalysts comparison was based on results obtained after 24 hours of time-on-stream The following catalysts were prepared in the same manner and with the same loading of cobalt and ruthenium, but different alumina supports.

Catalyst 1:

(Ru-Promoted Cobalt F-T Catalyst on CATAPAL B Alumina with 20 wt % Cobalt and 0.5 wt % Ruthenium)

Preparation Procedure:

Catapal B alumina from Condea/Vista in the boehmite form was calcined at 500° C. for 10 hrs to convert it to γ-alumina. It was then presieved to 400–170 mesh (or particle size range greater than 38 microns and lower than 88 microns).

The γ-alumina was impregnated with an aqueous solution of cobalt nitrate $[Co(NO_3)_2 6H_2O]$ and ruthenium (III) nitrosylnitrate $[Ru(NO)(NO_3)_3 xH_2O]$ using an appropriate quantity for incipient wetness (ca. 1.2 ml/g) with the desired loading of Co. The catalyst precursor was then dried in air at 115° C. for 5 hours and calcined in air at 300° C. for 2 hours (heating rate of ca. 1° C./min to 300° C.).

Reduction Procedure before Reaction:

The catalyst was reduced in a pure hydrogen flow of 3000 cc/g/hr by heating at 1° C./min to 350° C. and holding for 10 hrs.

Each of the following catalysts 2–5 were prepared in the same manner as catalyst 1. The specific supports employed in catalysts 2–5 were as follows:

Catalyst 2:

PURAL SB support supplied by Condea/Vista. The PURAL SB was produced by Condea/Vista in a manner similar to CATAPAL B, but at a different plant using a blending process.

Catalyst 3:

The support, PURAL SB1, was also supplied by Condea/Vista and was identical to PURAL SB except that the PURAL SB1 support did not contain titanium.

Catalyst 4:

The support, PURALOX DP/L3, was also supplied by Condea/Vista and was identical to PURAL SB except that the PURALOX DP/L3 support was doped with 2.8% by weight of lanthanum oxide ($La_2O_3$) and precalcined by the manufacturer at conditions similar to those used for Catalysts 1–3 in order to obtain a comparable surface area (200–250 $m^2/g$).

Catalyst 5:

The support, PURALOX DP/B3, was also supplied by Condea/Vista and was identical to PURAL SB except that the PURALOX DP/B3 support was doped with 2.7% by weight of barium oxide (BaO) and precalcined by the manufacturer at conditions similar to those used for Catalysts 1–3 in order to obtain a comparable surface area (200–250 $m^2/g$).

The particular CATAPAL B support material employed in Catalyst 1 was determined to contain an amount of titania "impurity" of about 1000 ppm by weight (expressed as ppm by weight of titanium) which was incidentally added, as part of the Ziegler Process, prior to the crystallization of the boehmite. The BET surface area of the CATAPAL B alumina calcined at 500° C. for 10 hours was 221 m$^2$/g. In contrast, the particular PURAL SB support material employed in Catalyst 2 had been formed by a blending process and was found to contain only about 500 ppm of titanium. The BET surface area of the PURAL SB alumina calcined at 500° C. for 10 hours was 204 m$^2$/g. The particular δ-alumina support, PURAL SB1, employed in Catalyst 3 was specially produced for us by Condea/Vista. The PURAL SB1 was identical to PURAL SB except that special efforts were made to prevent the addition of titanium. An elemental analysis showed that the PURAL SB1 support contained only 7 ppm of titanium. The BET surface area of the PURAL SB1 alumina calcined at 500° C. for 10 hours was 209 m$^2$/g.

The particular γ-alumina support, PURALOX DP/L3, employed in Catalyst 4 was specially produced for us by Condea/Vista. The PURALOX DP/L3 was identical to PURAL SB except that the PURALOX DP/L3 support was doped with lanthanum and precalcined by the manufacturer at conditions similar to those used for Catalysts 1–3 in order to obtained a comparable surface area. An elemental analysis showed that the PURALOX DP/L3 support contained only 2.8% by weight of lanthanum oxide (La$_2$O$_3$) and 1865 ppm by weight of titanium oxide (TiO$_2$). Its BET surface area was 201 m$^2$/g.

The particular γ-alumina support, PURALOX DP/B3, employed in Catalyst 5 was also specially produced for us by Condea/Vista. The PURALOX DP/B3 was identical to PURALOX DP/L3 except that the PURALOX DP/B3 support was doped with barium and precalcined by the manufacturer at conditions similar to those used for Catalysts 1–3 in order to obtained a comparable surface area. An elemental analysis showed that the PURALOX DP/B3 support contained only 2.7% by weight of barium oxide (BaO) and 40 ppm by weight of titanium oxide (TiO$_2$). Its BET surface area was 226 m$^2$/g.

Figure 2:
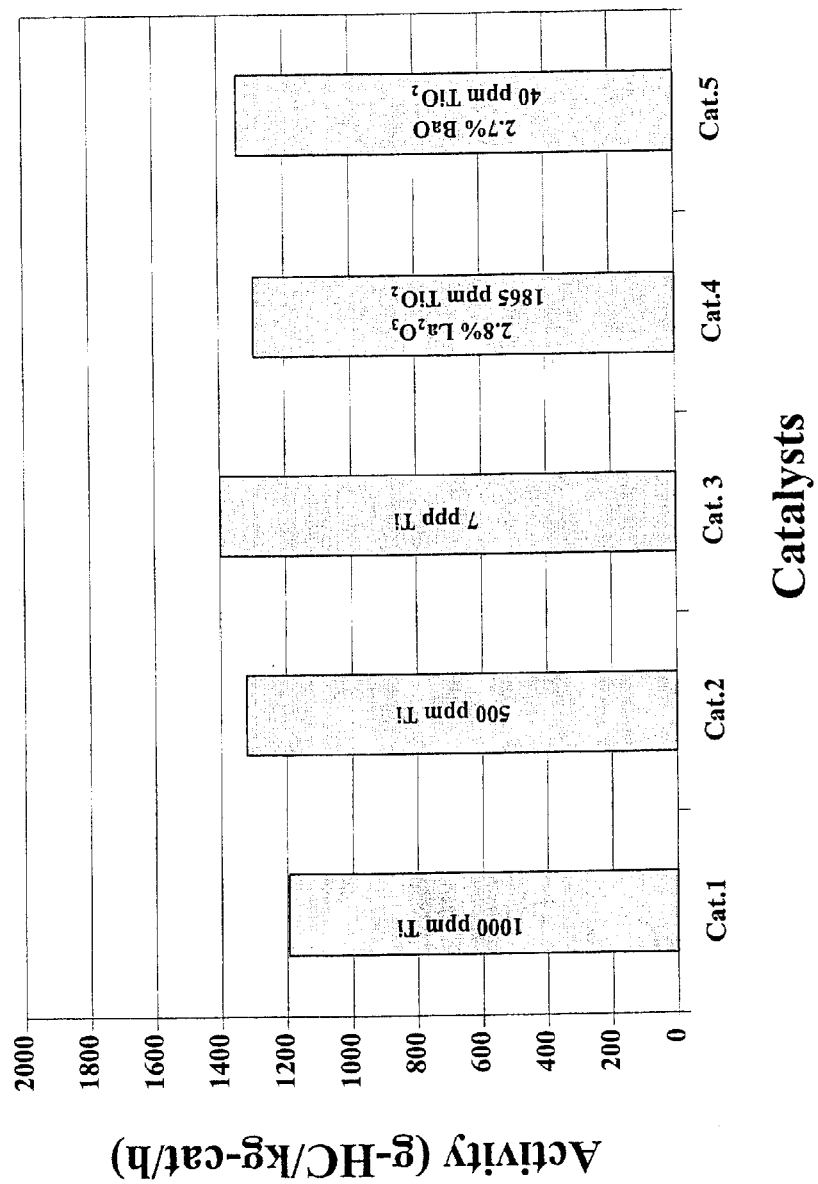
FIG. 2 provides a graph comparing the Fischer-Tropsch synthesis performances in a slurry bubble column reactor of promoted cobalt catalysts supported on non-doped, lanthanum-doped and barium-doped aluminas.

Catalysts 1–5 were tested in a slurry bubble column reactor. Table 1 and FIG. 2 show the activities (expressed in g-HC/kg-cat/hr) exhibited by each catalyst after its first 24 hours of use. A comparison of catalysts 1–3 illustrates the detrimental effect of titania on the activities of ruthenium promoted cobalt-on-alumina catalysts. As the amount of titania in the support increased, the activity of the catalyst declined from about 1400 for Catalyst 3, to about 1322 for Catalyst 2, and to about 1195 for Catalyst 1.

However, doping the alumina with lanthanum is believed to have reversed the effect of titanium. Catalyst 4 contained about the same amount of titanium as Catalyst 1, but its activity was, within experimental error, as high as those of Catalysts 3 and 4 which contained lower amounts of titanium.

The Catalyst 5 support contained almost no titanium, but was doped with about 3% barium oxide. The activity of this BaO doped catalyst was, within experimental error, almost identical to that of Catalyst 4.

In addition to these desirable and surprising results, a comparison of the selectivities of the five catalysts (see Table 1), shows that the doping of the alumina had no effect on catalyst selectivity. Within experimental error, the selectivities of the five catalysts for methane and C$_5$+ would be considered identical.

Thus, lanthanum or barium doping of the alumina support unexpectedly and surprisingly provides not only a higher stability for the catalyst but also a higher activity for Fischer-Tropsch synthesis, without any negative effect on the selectivity.

TABLE 1

EFFECT OF SUPPORT DOPANTS - SBCR SUMMARY DATA
(FIRST 24 HOUR AVERAGE)

| CATALYST # | ALUMINA | DOPANTS | CATAL. WEIGHT (g) | TEMP. (° C.) | CO CONV. (%) | THC (g-HC/kg-cat/hr) | SELECTIVITIES (% C) | | |
|---|---|---|---|---|---|---|---|---|---|
| | | | | | | | CH$_4$ | C$_5$$^+$ | CO$_2$ |
| Cat. 1 | Catapal B | Ti, 1000 ppm | 23.5 | 230.4 | 35.8 | 1195.0 | 7.8 | 82.5 | 0.9 |
| Cat. 2 | Pural SB | Ti, 500 ppm | 21.5 | 229.9 | 36.3 | 1322.4 | 8.5 | 81.9 | 0.7 |
| Cat. 3 | Pural SB-1 | Ti, 7 ppm | 15.1 | 230.9 | 27.1 | 1399.8 | 8.4 | 80.5 | 0.7 |
| Cat. 4 | Puralox DP/L3 | La$_2$O$_3$, 2.8%; TiO$_2$, 1865 ppm | 15.1 | 230.2 | 25.1 | 1294.7 | 8.2 | 80.7 | 0.7 |
| Cat. 5 | Puralox DP/B3 | BaO, 2.7%; TiO$_2$, 40 ppm | 15.1 | 230.7 | 26.0 | 1342.4 | 8.3 | 80.7 | 0.6 |

Reaction Conditions: Pressure = 450 psig; Flow Rates (SLPH): H$_2$ = 240, CO = 120, N$_2$ = 540.

Thus, the present invention is well adapted to carry out the objects and attain the ends and advantages mentioned above, as well as those inherent therein. While the invention has been described with a certain degree of particularity, it is manifest that many changes may be made without departing from the spirit and scope of this disclosure. It is understood that the invention is not limited to the embodiments set forth herein for purposes of exemplification.

What is claimed is:

1. A Fischer-Tropsch catalyst for Fischer-Tropsch hydrocarbon synthesis in a Fischer-Tropsch reaction system, said Fischer-Tropsch catalyst comprising:

a γ-alumina support;

an amount of cobalt, supported on said γ-alumina support, effective for said Fischer-Tropsch hydrocarbon synthesis in said Fischer-Tropsch reaction system; and at least one promoter on said γ-alumina support with said cobalt, said γ-alumina support having an internal structure comprising γ-alumina, at least 500 ppm of titania, expressed as elemental titanium and based on the total weight of said γ-alumina support, and an amount of a dopant selected from the group consisting of a lanthanum dopant, a barium dopant, and combinations thereof and wherein said amount of said dopant is an amount effective for increasing both the activity and the thermal stability of said catalyst for said Fischer-Tropsch hydrocarbon synthesis in said Fischer-Tropsch reaction system.

2. The Fischer-Tropsch catalyst of claim 1 wherein said one promoter is ruthenium.

3. The Fischer-Tropsch catalyst of claim 1 wherein said amount of said dopant present in said internal structure of said γ-alumina support is in the range of from about 1% to about 5% by weight based on the total weight of said γ-alumina support.

4. The Fischer-Tropsch catalyst of claim 1 wherein said amount of said dopant present in said internal structure of said γ-alumina support is in the range of from about 2% to about 3% by weight based on the total weight of said γ-alumina support.

5. The Fischer-Tropsch catalyst of claim 1 wherein said γ-alumina support is produced from aluminum alkoxide which is hydrolyzed to produce an alumina product and wherein said dopant is incorporated in said γ-alumina support by adding a dopant alkoxide to, and co-hydrolyzing said dopant alkoxide with, said aluminum alkoxide in an amount effective to yield said amount of said dopant in said internal structure of said γ-alumina support.

6. The Fischer-Tropsch catalyst of claim 1 wherein:

said γ-alumina support is produced from synthetic boebmite and said amount of said dopant is added to said γ-alumina support prior to crystalizing said synthetic boebmite.

* * * * *